US008999319B2

(12) United States Patent
Wise et al.

(10) Patent No.: US 8,999,319 B2
(45) Date of Patent: Apr. 7, 2015

(54) **ORAL VACCINATION OF FISH WITH LIVE ATTENUATED *EDWARDSIELLA ICTALURI* VACCINES**

(75) Inventors: David J. Wise, Scott, MS (US); Terrence Greenway, Leland, MS (US); Todd Byars, Belzoni, MS (US)

(73) Assignee: Mississippi State University, Mississippi State, MS (US)

( * ) Notice: Subject to any disclaimer, the term of this patent is extended or adjusted under 35 U.S.C. 154(b) by 0 days.

(21) Appl. No.: 13/261,536

(22) PCT Filed: Jun. 9, 2011

(86) PCT No.: PCT/US2011/001047

§ 371 (c)(1), (2), (4) Date: Mar. 8, 2013

(87) PCT Pub. No.: WO2011/155998

PCT Pub. Date: Dec. 15, 2011

(65) Prior Publication Data

US 2013/0164331 A1 Jun. 27, 2013

Related U.S. Application Data

(60) Provisional application No. 61/397,289, filed on Jun. 9, 2010.

(51) Int. Cl.

| | |
|---|---|
| ***A01N 63/00*** | (2006.01) |
| ***A61K 39/02*** | (2006.01) |
| ***A01K 61/02*** | (2006.01) |
| *A61K 39/00* | (2006.01) |

(52) U.S. Cl.

CPC ............... *A61K 39/025* (2013.01); *A01K 61/02* (2013.01); *A61K 2039/522* (2013.01); *A61K 2039/542* (2013.01); *A61K 2039/552* (2013.01); *A61K 2039/55566* (2013.01)

(58) Field of Classification Search

None

See application file for complete search history.

(56) References Cited

U.S. PATENT DOCUMENTS

| | | | | |
|---|---|---|---|---|
| 6,019,981 | A * | 2/2000 | Klesius et al. | 424/234.1 |
| 2010/0092431 | A1 * | 4/2010 | Liles et al. | 424/93.6 |

* cited by examiner

*Primary Examiner* — Brian J Gangle

(74) *Attorney, Agent, or Firm* — Lawrence Arthur Schemmel

(57) ABSTRACT

The present invention is directed to a novel live attenuated isolate and sub-isolets thereof of a strain of the pathogen *Edwardsiella ictaluri* for protecting fish from ESC infection or disease, a vaccine composition comprising the isolet, a method of oral delivery of the vaccine and any vaccine, and an apparatus designed to effectively mix the vaccine with fish feed and deliver the vaccine to fish.

23 Claims, 3 Drawing Sheets

Diagram of Mixing / Delivery Apparatus: Mixing Hopper is mounted over a conventional Blower type feed delivery apparatus

ORAL VACCINATION OF FISH WITH LIVE ATTENUATED *EDWARDSIELLA ICTALURI* VACCINES

CROSS-REFERENCE TO RELATED. APPLICATION

This application claims priority from U.S. Provisional Patent Application Ser. No. 61/397,289 filed Jun. 9, 2010. The entirety of that provisional application is incorporated herein by reference.

STATEMENT OF GOVERNMENT SUPPORT

This invention was made with government support under 58-6402-7-190 awarded by the USDA Agricultural Research Service. The government may have certain rights in the invention.

FIELD OF THE INVENTION

This invention relates to the field of vaccinating fish, with emphasis on all species of catfish that are or may be susceptible to enteric infections, and more specifically to vaccinating such fish with novel live attenuated vaccines and by new methods of oral delivery of the vaccines.

BACKGROUND OF THE INVENTION

One of the most costly diseases that affects channel catfish (Ictalurus punctatus) and the channel catfish industry is enteric septicemia of catfish (ESC). ESC is caused by a gram negative enteric bacterium identified as *Edwardsiella ictaluri* (*E. ictaluri*). The exact economic impact of this disease is unknown but is estimated to cost the industry 30 million dollars per year. Aside from morbidity and mortality resulting from *E. ictaluri* infection, the disease has an indirect effect on growth due to the implementation of restricted feeding practices designed to prevent or slow infection rates. Our research has demonstrated that oral ingestion of the pathogen is one of the primary routes of infection and that withholding feed from fish when environmental conditions are conducive for infection can prevent or dramatically reduce ESC-related mortality. While effective in preventing disease, this practice dramatically reduces production due to lost feed days.

A more attractive method of disease control is through vaccination. Many attempts have been made to vaccinate fish against ESC using simple killed bacterin preparations. While effective in controlling bacterial diseases in salmonids, bacterin-type vaccines (delivered orally or by bath immersion) to control ESC have been for the most part unsuccessful. Failure to successfully immunize fish has been attributed to poor antigen uptake during bath immersion and/or the inability of killed vaccines to elicit cellular immunity necessary to protect fish against an intracellular bacterial pathogen such as *E. ictaluri*. To overcome these limitations, an attenuated *E. ictaluri* vaccine has been developed using prior published art/technology. The vaccine was developed by successive passage of a wild-type virulent *E. ictaluri* isolate on media containing increasing concentrations of rifamycin. Rifamycin resistance causes mutation in the lipopolysaccharide O-side chain and diminished virulence. This methodology for attenuation by serial passage is well-known and based on procedures used to produce live attenuated vaccines for brucellosis in cattle [Vet. Micro. 28, 171-188 (1991)].

Attenuated vaccines have advantages over killed bacterin vaccines for several reasons: 1) they are living and invasive, thereby facilitating vaccine uptake; 2) they establish low-grade infections resulting in the stimulation of cellular immunity and typically establish longer-lasting immunity. A disadvantage of live vaccines is that they can be associated with some level of virulence and can result in mortality if delivered to an immuno-incompetent or immuno-suppressed host.

U.S. Pat. No. 6,322,793 (Vanderheijden, et al.) provides an attenuated avirulent recombinant vaccine against channel catfish virus (CCV) comprising deletion of gene 50 which encodes a secreted glycoprotein. U.S. Pat. No. 6,350,454 (Thune) and U.S. Pat. No. 6,010,705 (Thune, et al.) disclose a live attenuated *Pasteurella piscicida* and *E. ictaluri* vaccine, respectively, for fish. Another such attenuated ESC vaccine as described above is commercially available and marketed under the trade name AQUAVAC-ESC™ (Intervet/Schering Plough, U.S. Pat. No. 6,019,981 (Klesius, et al.)). According to label directives, the vaccine is administered by bath immersions to catfish seven (7) days or older. To conform to industry practices, the vaccine is typically administered to catfish fry between 7-12 days of age-post hatch when fish are transferred from the hatchery to rearing ponds. The current vaccination strategy has three (3) primary drawbacks resulting in marginal efficacy in terms of disease protection and economic returns: 1. Fish are being vaccinated at a stage in development that prevents the development of an optimal immune response. Studies in other laboratories suggest 7-10 day old fry are not fully immunocompetent which marginalizes the full potential of the vaccination; 2. Optimal immunity resulting from vaccination does not coincide with the onset of ESC because of the seasonal occurrence pattern of the disease. Studies conducted in our laboratory have demonstrated that immunity resulting from vaccination with AQUAVAC-ESC™ is short-lived and begins to wane after 1 month. In a typical production season, fry are produced and vaccinated approximately 2-3 months prior to observance of optimal environmental temperature windows favorable for the emergence of ESC. This temporal relationship between vaccination and the onset of disease dramatically decreases the efficacy of the vaccination; and 3. Poor survival of vaccinees prior to the emergence of ESC increases the unit cost of vaccination and decreases net returns on vaccine investment. It is typical for commercial producers to experience on average 20% mortality in newly-stocked fry and young fingerlings from a variety of non-disease related causes. These types of losses are commonly referred to as black-hole losses and are thought to occur shortly (within 3 weeks) after fry are transferred from the hatchery to the pond. In addition, it is common for 3-5% of the ponds used in the production channel catfish fingerlings to experience 100% mortality due to unknown causes or oxygen depletions. These losses increase the unit cost of vaccination, since the cost of vaccinating fry that do not survive the initial stages of production must be distributed across the surviving vaccinates. In addition, with current vaccination practices, much apprehension is generated due to the potential occurrence of vaccine-induced mortality. In laboratory trials, bath vaccination with live attenuated *E. ictaluri* vaccines has resulted in significant mortality starting 3-7 days post-vaccination. These responses have been variable and are thought to be related to the young age of fry at vaccination. Other trials have shown that these adverse reactions to vaccination decreased with increasing fry age. No adverse effects to vaccination have been shown in fish over 30 days of age. Therefore, oral in-pond vaccination of fish, specifically of catfish, utilizing the present invention will not only improve efficacy as stated above but also increase the safety of vaccination.

A need exists in the field of preventative and protective fish vaccination for a new and efficient methodology for vaccinating fish to protect against such diseases. The present invention provides such a set of isolets, method of administration, and apparatus for delivery of vaccine. The present invention in a preferred embodiment utilizes at least one novel live attenuated *Edwardsiella ictaluri* isolate for vaccination of fish and a new and distinctive method of oral delivery and administration of any vaccine to fish, specifically catfish, for preventing disease and decreasing mortality. The present invention further provides an apparatus designed for delivering any vaccine utilizing the new method of oral vaccine delivery.

SUMMARY OF THE INVENTION

The present invention provides for a novel live attenuated *Edwardsiella ictaluri* isolate for use as a vaccine for treating fish against *E. ictaluri* infection and for a new method of orally administering or delivering such vaccine, or any vaccine orally, as well as a novel apparatus for, efficiently and effectively delivering the vaccine to the fish.

Through the inventors' research, evaluating the pathogenesis of *Edwardsiella ictaluri* infection, the inventors investigated the potential of orally delivering attenuated vaccines to fish. The present invention in a preferred embodiment shows that the research results demonstrate that fish can be effectively immunized and protected against *E. ictaluri* infection by a single oral administration of the vaccine. This new method of oral delivery can be utilized for the novel vaccine or any vaccine. The advantages of oral vaccine delivery are multifold. The practice allows for mass vaccination of fish in ponds, a scenario not feasible with bath immersion vaccination strategies. Moreover, in-pond vaccinations via oral route secures a more fully immunocompetent population at the time of vaccination. Timely administration of the vaccine can broaden the protective window when peak immunity coincides with environmental conditions conducive for enteric septicemia (ESC) outbreaks. Oral delivery of low virulent strains of *Edwardsiella tarda*, potentially suitable for vaccine use, was also shown effective in stimulating the production of anti-*E. tarda* antibodies. This addendum to this body of research shows that live attenuated *E. tarda* vaccines can also be delivered orally and is a component of the embodiments of the present invention.

The novel process of the present invention begins with the development of a novel attenuated *E. ictaluri* isolate using prior art according to procedures by Schurig et al. (1991). These procedures have been modified to allow for mass and rapid attenuation of virulent *E. ictaluri* isolates. This allows for the production of polyvalent vaccines on a yearly basis to account for heterogenicity and antigenic variations between pathogen strains over time. This new process of vaccinating fish involves a simple yet novel approach of incorporating a live attenuated *E. ictaluri* vaccine, or any live attenuated vaccine, into commercially available feeds. The vaccine feed/mixture is prepared by adding about 220 ml of diluted vaccine to about 1 kg of feed (100 ml/lb of feed) to deliver a minimum of $1\times10^{+6}$ CFU/gram of feed. The concentration of the dilute vaccine can be adjusted to achieve a desired moisture consistency of the prepared feed. For example, if less liquid is desired the initial vaccine dilution is lowered to deliver the same target dose. To ensure equal distribution of dilute vaccine, no less than 50 ml of fluid should be added to 1 lb of feed. The vaccine feed mixture is mechanically mixed for 2-5 minutes and administered to fish. A single vaccine application (feeding) provides optimal immunity and is to be delivered approximately 30-60 days prior to anticipated ESC outbreaks. The vaccine/feed mixture is fed to fish at a rate of approximately 3% body weight. This delivery methodcan also be applied to feeds utilizing spray or aerosol technologies and used against other enteric diseases of fish. For example, the development processes and methods of oral delivery of the present invention are applicable to the development and administration of vaccines against *Edwardsiella tarda* infection. *Edwardsiella tarda* is an enteric bacterial fish pathogen of channel catfish, blue catfish, and blue x channel catfish hybrids and is closely related to *Edwardsiella ictaluri.*

The present invention provides for a new live attenuated *Edwardsiella ictaluri* isolate, incorporation of the isolet and any live attenuated enteric vaccine into commercially-available feeds, a method of oral delivery of the new vaccine and any enteric vaccine(s) to fish, and a feed delivery system comprising an apparatus to mix, moisten, and deliver the vaccine and any vaccine/feed composition to fish and to ensure viability to the attenuated isolate.

With the foregoing and other objects, features, and advantages of the present invention that will become apparent hereinafter, the nature of the invention may be more clearly understood by reference to the following detailed description of the preferred embodiments of the invention and to the appended claims.

BRIEF DESCRIPTION OF THE DRAWINGS

These drawings accompany the detailed description of the invention and are intended to illustrate further the invention and its advantages. The drawings, which are incorporated in and form a portion of the specification, illustrate certain preferred embodiments of the invention and, together with the entire specification, are meant to explain preferred embodiments of the present invention to those skilled in the art.

DETAILED DESCRIPTION OF THE INVENTION

Figure 1:
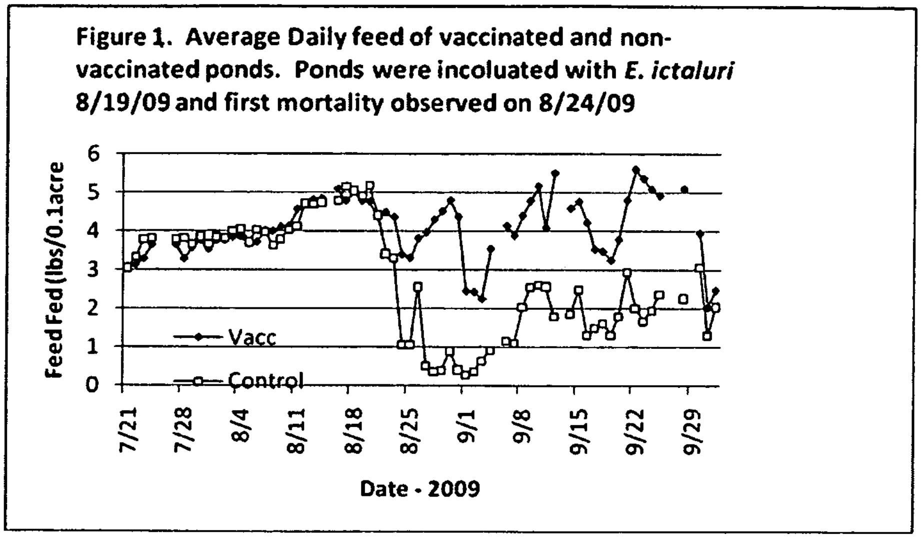
FIG. 1 is a graphical illustration of field trial results of the average daily feed of vaccinated and non-vaccinated ponds and shows feeding activity changes in the two groups when ponds were inoculated with the new attenuated isolate using the method of the present invention on Aug. 19, 2009.

The present invention provides for a novel live attenuated isolate, and related sub-isolets, of *E. ictaluri* that is resistant to rifamycin to protect fish from infection, specifically catfish, against deadly strains of *E. ictaluri*. Further, it provides a novel method of oral delivery to fish of any vaccine that more effectively protects the fish, as well as an apparatus for delivering and administering the feed/vaccine composition.

While it has been demonstrated that current fish vaccination methods increase production efficiency, the level of efficacy is considered marginal in terms of disease protection and economic returns. Marginal vaccine efficacy is attributed to the age of fish at vaccination, short lived immunity, and non-disease related mortality of vaccinees resulting in an increase in the unit cost of vaccination. Through research, the inventors discovered a new attenuated isolate, a new method of oral delivery of any live attenuated fish vaccine, and a novel apparatus to mix and deliver the new vaccine that proved to be highly effective in protecting fish from ESC. The results demonstrate that fish can be immunized and protected against *E. ictaluri* infection by a single oral administration of the vaccine by the new method of vaccine delivery. The new isolate provides effective vaccination of fish and this novel method of oral delivery allows for the in-pond vaccination of older and fully immunocompetent fish and the timely administration of vaccines where peak immunity coincides with conditions conducive for ESC epizootics. Moreover, the novel isolate, composition, and method of oral delivery also effectively protects fish against infection from virulent *Edwardsiella tarda* and any other enteric infection or disease. The isolate itself is effective against infection and can be administered via multiple delivery methods including, but not limited to, immersion, injection, and oral delivery. The new isolate, vaccine oral delivery method, and mixing/delivery apparatus also minimize the costs associated with the vaccination of fish that die from non-disease related causes.

The invention is explained in detail by the examples herein and it should be apparent to those of ordinary skill in the art that one or more of the sub-isolates of the attenuated culture S97-773-340X may be utilized and remain within the scope of the invention. Moreover, the vaccine composition is effective for use and is contemplated for use in protecting both free-swimming and farm-raised catfish. The terms vaccine and vaccine composition are defined herein in their broadest sense to refer to any biological agent able to be administered and capable of stimulating an immune response in a fish given the vaccine or composition. The vaccine or composition of the invention may comprise at least one live attenuated isolate of *E. ictaluri* that is resistant to rifamycin. As used herein and in the claims, a protective dosage is defined as that amount of an attenuated isolet or vaccine composition which, when administered to a fish, induces a level of immunity in a population of fish sufficient to reduce the susceptibility of the fish to pathogen infection such as ESC to a statistically significant degree such that the level of protection for the population is statistically significantly higher than that of a control group that is unvaccinated and unprotected.

Procedures for Preparing and Delivering Vaccine Feed Mixtures:

The vaccine can be prepared for oral delivery from a fresh culture of an attenuated isolate or from frozen or freeze dried cultures that serve as a working stock vaccine. Frozen/freeze dried cultures are developed for the purpose of long-term storage and off-site delivery of live attenuated vaccines. Frozen/freeze dried vaccines will be collectively referred to as "stored vaccines". The process for oral vaccination is described in sequential order and an example is outlined in Example 1. The new attenuated isolate and sub-isolates are currently stored at the National Warmwater Aquaculture Center in Stoneville, Miss. and will be transferred to a commercial storage facility and/or a sample deposited at a permanent facility at some time in the future for production and protection, respectively.

The attenuated cultures S97-773-340X and S97-773-340X2 were deposited with the American Type Culture Collection (ATCC), 10801 University Boulevard, Manassas, Va., 20110-2209, USA, on Sep. 11, 2014, and received ATCC Designation Deposit Nos. PTA-121592 and PTA-121593, respectively.

I. Description of the Process for Preparing Live Attenuated Oral Vaccines.

Preparation of Vaccine from Fresh Cultures:

The vaccine can be prepared from a fresh culture or from cultures that have been freeze-dried or frozen for long-term storage. The vaccine is diluted in any suitable diluent (i.e., preferably unchlorinated water containing about 0.1-0.3% saline) that maintains viability of the attenuated isolate to deliver a minimum $1\times10^{+6}$ CFU/gram of wet feed. Sodium chloride may also be added if necessary. The diluted vaccine is mixed with feed at a rate of 100 ml dilute vaccine/1 lb of feed.

Emulsification:

The dilute vaccine can be emulsified with oil to prevent desiccation of vaccine feed mixture. Under extreme conditions (excessive long application times or high temperatures) this process may be necessary to maintain viability of the live attenuated vaccine in feed. Just prior to mixing the vaccine with feed, an emulsion is made from the dilute or dilute-stabilized vaccine with 20% fish or vegetable oil containing long chain unsaturated fatty acids. Tween 20 is added as an emulsifying agent at a rate of 200 μl/100 ml of dilute vaccine. The mixture is mixed using a high speed mixer until the vaccine is emulsified. The emulsified vaccine is added to a commercially-prepared floating catfish feed at a rate of 100 ml emulsified vaccine/1 lb of feed.

Mixture of Vaccine/Feed:

The dilute vaccine is added to feed at a rate of 100 ml vaccine/1 lb of feed to deliver the target dose. The vaccine/feed mixture is continually mixed to ensure equal dispersion until excess liquid is absorbed.

Delivery of Oral Vaccine:

The vaccine is fed to apparent satiation (approximately 3-5% body weight). To ensure maximum feed consumption and coverage to individual fish within the population, fish are withheld from feed two (2) days prior to vaccination. The amount of feed needed to vaccinate a pond population of fish is determined by averaging the daily feeding rate over the last 5-7 days. This value gives an estimated amount of feed to be mixed with the dilute vaccine. The mixture should be completely fed to fish within 15 minutes.

II. Process Delivering Prepared Live Attenuated Oral Vaccines.

Small-Scale Vaccination Procedures:

Vaccine/feed preparations of less than 50 lbs can be mixed using a mixer, for example a portable 200 lb capacity mixer comparable to a cement mixer. The feed is added to the mixer and mixed as the dilute vaccine is slowly added. The contents are mixed until excess moisture is absorbed by the feed (typically 1-2 minutes). The vaccine feed mixer can be fed by hand (provided the feed can be delivered within 15 minutes) or transferred to a commercial-type blower feeder and broadcast to the pond. If delivery is expected to exceed 15 minutes, the moisture of the vaccine feed mixture must be maintained to ensure viability of the vaccine. This can be accomplished with the unchlorinated water diluent using a hand-held or other comparable spray device.

Large-Scale Vaccination Procedures:

Oral vaccination of fish produced on large-scale commercial operations requires a specialized apparatus to mix and deliver the oral vaccine. Due to the volume of feed required to vaccinate large populations of fish, the vaccine cannot be mixed in multiple small batches then transferred to a commercial blower type feeder and delivered to fish within 15 minutes. A specialized apparatus is utilized to accommodate the preparation and delivery of large vaccine/feed batches.

III. Description of Mixing, Delivery, and Spray Apparatus.

A special feed mixing and delivery apparatus was developed to allow for the commercial scale oral vaccination of fish using the new isolet and vaccine compositions. This novel apparatus consists of a seed coater or comparable device mounted with or over a fan type blower system to deliver the fish feed and vaccine (FIG. 1). The disclosed apparatus is designed to prepare 50 to 200 lb batches of dry feed. If larger volumes of feed are needed, the size of the feed hopper can be increased.

Mixing apparatus: The apparatus contains a primary cylindrical conical bottom chamber (for example, 30" diameter× 36" height) that serves as a hopper to hold bulk feed to be mixed with the vaccine. In the center of the hopper is positioned, for example, a 12-inch vertical auger centered in a 13-inch open-ended auger tube (with about a ½-inch clearance between the auger and the surrounding tube) fixed by supports. The tube height is approximately 6" below the top of the hopper and is fixed 3" above the conical bottom. The auger drive shaft is attached to the top and bottom of the hopper through bushings allowing for the free rotation of the auger within the stationary auger tube. The bottom shaft extends through the bushing and is fixed to a chain-driven or similar gear wheel that is driven by a gasoline or fuel-driven or electric motor, or comparable device. The conical bottom of the hopper directs feed to the bottom opening of the auger tube, allowing the feed to come in direct contact with the bottom blade of the auger. The auger drives the feed to the top of the auger top where it is deposited on the top of the bulk feed (payload). As feed is driven upward, feed at the bottom of the cylinder is forced into the auger tube/auger apparatus. This process continually circulates feed from the bottom to the top of the hopper allowing for complete mixing.

Delivery Apparatus:

The mixing apparatus is mounted over a feed delivery apparatus having a blower that blows the vaccine/feed mixture into the pond. A connecting exit chute is located on the conical side of the hopper that allows feed to be gravity fed from the mixing apparatus to the delivery apparatus. A sweeper arm is attached to the drive shaft (bottom of the mixing cylinder) to help direct the feed to the exit chute. After the feed is completely mixed and ready for application, an actuated gate allows feed to pass from the hopper (through the connecting exit chute) directly into the feed delivery chute. A fan-type blower driven by a motor propels the feed into the pond as the feed enters the feed chute. The rate of delivery is governed by the degree to which the gate is opened or closed.

Spray Apparatus:

If pond size and/or estimated feed time prevents delivery of feed within about 15 minutes, the mixing apparatus should contain a minimum 20-gallon tank and spray system to maintain the moisture content of the feed. The moisture content is defined as the moisture level of the original mixture. The spray system is typically operated by a 12-volt battery powered spray pump, but can utilize other power sources, and delivers fluid through a series of fine tip spray nozzles. The vaccine diluent (preferably unchlorinated water) or additional non-emulsified diluted vaccine can be used to moisturize the vaccine/feed admix in the hopper during feed delivery. The spray nozzles are calibrated to deliver approximately 3.0 ml of fluid/minute/pound of feed.

Experimental Results Completed

1. Laboratory trials using orally-delivered vaccines (Experiment 1 and 2)
2. Delivery methods (Delivery apparatus—FIG. 1)
3. Developed and tested attenuated *E. ictaluri* strain S97-773-340X2
   a. Laboratory Tests (Experiment 3)
   b. Field Tests (Experiment 4)

Experiment 1: Demonstration of an Oral Delivery Platform Using a Live Attenuated *E. ictaluri* Isolate Incorporated in Feed.

Demonstration of concept: Oral delivery of an attenuated strain of *E. ictaluri* is effective in inducing protective immunity in channel catfish against enteric septicemia of catfish (ESC).

Methods

Experimental Treatments:

Optimal oral doses were evaluated in channel catfish fingerlings 3-4 inches in length. Vaccination trials were conducted in 30 gallon aquaria containing approximately 22 L of oxygenated well water. Water temperature ranged between 26-27° C. Thirty (30) aquaria were each stocked with 20 channel catfish and assigned one of 5 treatments (6 replicates per treatment). Treatments consisted of fish fed a commercial catfish feed mixed with a non-diluted vaccine (1:0) and a 1:10, 1:50, and 1:100 dilution of the vaccine. The remaining 6 aquaria received feed only on the day of vaccination and served as non-vaccinated controls.

Feed Preparation and Vaccination:

Fish were vaccinated with a commercially-available frozen vaccine marketed under the trade name AQUAVAC-ESC™. At the time of vaccination, fish were consuming approximately 27 g feed/aquaria/day. On the day of vaccination, the vaccine was thawed to room temperature for approximately 1 h. Vaccine dilutions (0, 5, 10, 50, and 100 fold dilutions) were prepared using sterile BHI infusion broth and immediately mixed with feed at a rate of 100 ml vaccine/454 g of feed. The vaccine/feed admix was mixed until excess liquid was absorbed by the feed pellets and fed immediately to the fish. Each aquaria received 27 grams of feed mixed with 6 ml of vaccine of the appropriate dilution. Standard plate counts were performed on the undiluted vaccine as well as the vaccine/feed admix at vaccine dilutions of 0, 1:10, and 1:100.

Fish were not fed for two (2) days prior, to vaccination. Following vaccination, the fish were monitored daily for mortality and morbidity. Fish suitable for necropsy were evaluated to determine cause of death.

ESC Challenge:

ESC was induced in test fish by immersion exposure to a virulent culture of *Edwardsiella ictaluri* 30 days after fish were orally vaccinated. Fish were observed daily for 30 days and dead fish were recorded and removed from the aquaria. Cumulative daily mortality was analyzed by Analysis of Variance and treatment differences determined least significant differences (LSD) procedures. Relative percent survival was used to assess vaccine efficacy.

Results

The number of viable cells in the concentrated thawed vaccine was $2\times10^{+10}$ CFU/ml. Viable cell number in the vaccine/feed mixture was $2.5\times10^{+8}$, $1.0\times10^{+7}$, and $1.1\times10^{+6}$ CFU/g of wet feed for vaccine dilutions of 0, 1:10, and 1:100. With the exception of two aquaria, fish consumed a majority of feed offered. Before fish were exposed to the virulent culture of *E. ictaluri*, no mortalities were observed following vaccination. Exposure of fish to virulent *E. ictaluri* was shown to induce ESC and *Edwardsiella ictaluri* was cultured from all necropsied fish. All vaccinated treatments had significantly lower mortality compared to non-vaccinated control fish. Mortality among vaccinated fish was similar, indicating a 1:100 dilution of the vaccine was equally as effective as the non-diluted vaccine (Table 1). Mortality of control fish was 56.3%, while vaccinates exhibited mortality ranging from 6.7 to 18.3%, resulting in an RPS from 67.6 to 84.2%. These data indicate oral delivery by the methods of the present invention of an attenuated strain of *E. ictaluri* is effective in inducing protective immunity against ESC.

TABLE 1

Demonstration of an oral delivery platform using a live attenuated *E. ictaluri* isolate incorporated in feed. Fish were fed various vaccine/feed mixtures to apparent satiation and exposed to a virulent culture of *E. ictaluri* 30 days after oral delivery. Table data represents cumulative mean mortality of each replicate, treatment means and relative percent mortality. Mean cumulative percent mortality was subjected to analysis of variance followed by least significant differences test. Treatment means followed by different superscripts are significantly different. Relative percent survival was determined by amend and used to evaluate treatment efficacy.

| | | Vaccine dilution for oral vaccine treatments | | | | |
|---|---|---|---|---|---|---|
| Replicate | Control | 1:0 | 1:5 | 1:10 | 1:50 | 1:100 |
| R1 | 67 | 13 | 15 | 9 | 10 | 14 |
| R2 | 67 | 3 | 32 | 6 | 40 | 19 |
| R3 | 70 | 10 | 11 | 5 | 30 | 23 |
| R4 | 45 | 7 | 0 | 7 | 13 | 23 |
| R5 | 62 | 13 | 14 | 7 | 10 | 10 |
| R6 | 30 | 7 | 11 | 7 | 7 | 7 |
| MEAN | $56.3^{a}$ | $8.9^{b}$ | $13.8^{b}$ | $6.7^{b}$ | $18.3^{b}$ | $16.0^{b}$ |
| RPS | — | 84.2 | 75.6 | 88.1 | 67.1 | 71.6 |

Note:
Numbers with different superscripts are statistically different.

Experiment 2: Comparison of Immersion and Oral Vaccination Applicable to Current Industry Practices.

Objective:

To evaluate the effectiveness of a novel oral vaccination strategy compared to immersion vaccination practices in current use by the channel catfish industry.

Methods

Experimental Treatments:

Channel catfish, obtained from a single population, were vaccinated as fry by immersion exposure or as fingerlings by oral delivery. Channel catfish sac-fry (1-3 days of age post-hatch) were obtained from a commercial catfish hatchery and placed in a single rearing trough. At the swim-up stage of development, fry were fed hourly a commercial trout starter diet. Fry were vaccinated 10-12 days of age post-hatch (in accordance to label directives and current industry practices) by immersion exposure with a commercially-available live attenuated ESC vaccine (AQUAVAC-ESC™). Twelve (12) separate groups of fry (1000 fish) were vaccinated and each group placed in 12, 100 L aquaria containing approximately 80 L of water. An additional 18 aquaria were stocked with non-vaccinated fry to serve as controls and oral vaccination treatments at the fingerling stage of development (timeline: 50 days after cohorts received immersion vaccination). Oral treatments consisted of controls (non-vaccinated) and fish vaccinated with a 1:10 and 1:100 dilution of vaccine in feed admix. At the time of 50 days post immersion vaccination, one-half of the immersion vaccination treatments (6 aquaria) received a secondary immunization via the oral route with a 1:100 diluted vaccine feed admix (immersion/oral boost). At this time, 12 aquaria of non-vaccinated fish were orally vaccinated with a 1:10 (n=6) and 1:100 (n=6) vaccine dilution (oral vaccination occurred 50 days after immersion vaccination). The remaining 6 aquaria were left unvaccinated and served as controls for the immersion and oral vaccine treatments.

Vaccine Preparation and Delivery:

The oral delivery method was evaluated using a commercially available vaccine (AQUAVAC-ESC™). Immersion vaccination procedures were in accordance with label directives. Approximately 70 g for fry (0.07 mg/fry) were placed in a 400 ml vaccine bath containing $8\times10^{+7}$ CFU/ml of water.

After 2 minutes, the vaccine bath was diluted 1:4 with hatchery well water. Fish were held in the dilute vaccine bath for an additional 30 min then transferred to the designated rearing aquaria. At the time of oral vaccination, fish were consuming approximately 7 g of feed/aquaria/day. Feed was prepared by diluting the thawed vaccine (AQUAVAC-ESC™) 1:10 and 1:100 with brain heart infusion media (BHI) and mixing the dilute vaccine with feed at a rate of 100 ml/454 g feed (1.5 ml to 7 g of feed). The vaccine feed admix was mixed until excess liquid was absorbed by the feed pellets and fed immediately. Following vaccination, fish were monitored daily for mortality and morbidity. Fish suitable for necropsy were evaluated to determine cause of death. Plate counts were performed on the concentrated thawed vaccine, vaccine bath, and on the 1:10 and 1:100 diluted vaccine feed mixture.

ESC Challenge:

ESC was induced by exposure to a virulent culture of *Edwardsiella ictaluri* 30 days after fish were orally vaccinated. Fish were observed daily for 30 days and dead fish were recorded and removed from aquaria. Cumulative daily mortality was analyzed by Analysis of Variance and treatment differences determined LSD procedures. Relative percent survival was used to assess vaccine efficacy.

TABLE 2

Comparison of oral and immersion vaccination practices. Disease was induced in test fish by exposing fish independently to two doses of virulent cultures of *Edwardsiella ictaluri*. Fish were fed various vaccine/feed mixtures to apparent satiation and exposed to a virulent field strain of *E. ictaluri* 30 days after fish received the oral booster. Table data represents cumulative mean mortality of each replicate, treatment means and relative percent mortality for each challenge dose. Mean cumulative percent mortality was subjected to analysis of variance followed by least significant differences test. Treatment mean followed by different superscripts are significantly different. Relative percent survival was determined by amend and used to evaluate treatment efficacy.

| Rep | Control | Immersion | Imm + Boost | Oral 1:10 | Oral 1:100 |
|---|---|---|---|---|---|
| | 8 ml Challenge Dose (PSEM = 0.03634) Percent Mortality | | | | |
| 1 | 50 | 53 | 17 | 10 | 14 |
| 2 | 43 | 53 | 12 | 13 | 14 |
| 3 | 44 | 21 | 21 | 20 | 9 |
| 4 | 52 | 20 | 23 | 10 | 17 |
| 5 | 34 | 21 | 15 | 7 | 17 |
| 6 | 57 | 29 | 21 | 7 | 21 |
| Mean | $46.7^{a}$ | $33.0^{b}$ | $18.0^{c}$ | $11.0^{c}$ | $16.3^{c}$ |
| RPS | — | 29.3 | 61.4 | 76.5 | 65.0 |
| | 16 ml Challenge Dose (PSEM = 0.03466) Percent Mortality | | | | |
| 1 | 88 | 39 | 21 | 10 | 10 |
| 2 | 68 | 45 | 14 | 10 | 14 |
| 3 | 69 | 48 | 20 | 27 | 15 |
| 4 | 68 | 28 | 26 | 7 | 33 |
| 5 | 65 | 59 | 10 | 7 | 25 |
| 6 | 60 | 50 | 23 | 3 | 17 |
| Mean | $69.4^{a}$ | $44.9^{b}$ | $19.1^{cd}$ | $10.7^{d}$ | $20.8^{c}$ |
| RPS | — | 35.3 | 72.4 | 84.6 | 70.1 |

Note:
Numbers with different superscripts are statistically different.

Results

Viable cells numbers in the vaccine/feed mixture was $3.0\times10^{+8}$ and $1.3\times10^{+7}$ CFU/g of wet feed. Feed consumption was below average but fish consumed over 75% of the feed offered. Before fish were exposed to the virulent culture of *E. ictaluri*, no mortalities were observed following vaccination. Exposure of fish to virulent *E. ictaluri* was shown to induce ESC and *Edwardsiella ictaluri* was cultured from necropsies. Similar trends in mortality were observed at the 8 ml and 16 ml challenge doses. Regardless of virulent challenge dose, all vaccinated fish had lower mortality than non-vaccinated fish. Delivery of the vaccine by immersion exposure, however, offered limited protection against *E. ictaluri* infection (not as effective as the oral method of delivery of the present invention). The RPS of orally-vaccinated fish was between 61.4 and 76.5 in the 8 ml challenge dose and between 70.1 and 84.6 in the 16 ml challenge dose. In comparison, the RPS of fish vaccinated by immersion exposure was 29.3 and 35.3 in the 8 ml and 16 ml challenge doses, respectively. The data also showed that immersion vaccination followed by an oral booster did not improve survival compared to fish that received a single oral vaccine dose. These data indicate that oral delivery of attenuated *E. ictaluri* vaccines of the present invention is superior to immersion vaccination practices currently used by the catfish industry.

Experiment 3: Evaluation of Newly Attenuated Isolates of *E. ictaluri* (S97-773-340 X, Y, P) as Potential Candidates for Vaccine Development.

Objective:

To evaluate the effectiveness of newly attenuated strains of *Edwardsiella ictaluri* in an oral delivery platform.

Methods

Attenuation Process:

A virulent isolate of *Edwardsiella ictaluri* (S97-773), collected from a natural ESC outbreak on a commercial fingerling farm in northwest Mississippi, was attenuated by successive passage on bacterial media containing increasing concentrations of rifamycin (Rif) according to modified procedures described by Schurig, et al. (1991). Multiple colonies were transferred with each passage. An isolate exhibiting growth on media containing incremental increases of Rif greater than 40 μg/ml was designated with a letter to identify potentially unique isolates. Isolates were successively transferred until growth was exhibited in the presence of 340 μg Rif/ml. Multiple isolates were transferred to BHI broth containing 340 μg Rif/ml and expanded for 24 h at 27° C. Cultures were frozen in 20% glycerol at −80° C. for storage and future testing.

Vaccine Screening and Development:

Three primary isolates, S97-774-340X (340X), S97-773-340Y (340Y) and S97-773-340P (340P), were evaluated for safety and efficacy. Tests were also conducted with the parental wild type isolate S97-773 for reference. Each frozen isolate was thawed to room temperature and 100 μl transferred to 9 ml BHI broth. After 24 h, 1 ml of the culture was expanded in 1000 ml of BHI broth (18 h @ 27° C.). Fish were exposed to the expanded cultures by bath immersion as an initial screening process. Twenty fish/aquaria were stocked in each aquaria and exposed to the attenuated isolates. For each isolate (340X, 340Y, and 340P) fish in 5 aquaria were each exposed to approximately $3.3\times10^{+3}$, $3.3\times10^{+4}$ and $3.3\times10^{+5}$ CFU/ml of water and fish in one aquaria were exposed to $3.3\times10^{+6}$ CFU/ml of water. Thirty days after exposure to the attenuated isolates, fish were exposed to a single dose of virulent *E. ictaluri.*

Evaluation of Potential Vaccine Candidates:

The attenuated strain shown safe and effective against *E. ictaluri* infection by immersion exposure was evaluated for potential as an oral vaccine. The potential vaccine candidate was expanded in 9 ml BHI broth and cultured for isolation on TSA blood agar plates. After incubation (48 h), five (5) randomly selected isolate colonies were expanded in 9 ml BHI broth and labeled 340X1, 340X2 . . . 340X5. Each culture was frozen in 20% glycerol at −80° C. for storage and future use.

To evaluate isolates for use as an oral vaccine, 46 aquaria were each stocked with 20 fish and acclimated for 2 weeks. Fish were fed once daily a 36% protein floating catfish diet. Each isolate tested (340X1 through 340X5) was expanded in 500 ml of BHI broth (20 h @ 27° C.). On the day of vaccination, each culture was diluted 1:10 and 1:100 with distilled water containing 1.0 g/L NaCl. Each isolate and dilution was mixed with feed at a rate of 100 ml per 454 g of feed. A separate vaccine/feed mixture was prepared for fish in each aquaria (3.3 ml dilute vaccine/15 grams feed). Fish from 8 aquaria were orally vaccinated with each of the 5 isolates—one-half of the aquaria received a 1:10 dilution of the vaccine/feed mixture and the remaining aquaria were vaccinated with a 1:100 dilution of vaccine/feed mixture. An additional 6 aquaria remained unvaccinated and served as controls. Two days prior to oral vaccination, fish were withheld from feed to ensure optimal feed consumption. Fish were fed to apparent satiation with feed consumption graded on a scale of 1 to 4 to estimate the total amount of feed fed. Fish were examined for 30 days to evaluate possible post-vaccination reactions. The posterior kidney of dead/moribund fish suitable from necropsy were cultured on TSA blood agar plates for the isolation of *E. ictaluri*: Bacterial colonies consistent, with *E. ictaluri* were additionally cultured on TSA blood agar plates containing 340 μg/ml Rif to identify the isolate used for vaccination.

Thirty (30) days after vaccination, fish were exposed to a virulent culture of *Edwardsiella ictaluri* to induce ESC. Fish from each aquaria were exposed to approximately $1\times10^{+6}$ CFU/ml for thirty minutes under static water conditions. After 30 min, the flow of water was resumed and fish examined daily for 30 days. Dead fish were recorded and removed from aquaria daily and necropsy was performed on fish suitable for diagnostic evaluation to determine cause of death. The posterior kidney and brain were cultured on TSA blood agar plates and dilute Mueller-Hinton plates for isolation of bacterial pathogens. Cumulative daily mortality was analyzed by Analysis of Variance and treatment differences determined by LSD procedures. Relative percent survival was used to assess vaccine efficacy in vaccine treatments.

Results:

The initial screening of the three (3) primary attenuated isolates, exhibiting growth on TSA blood agar plates, were evaluated for safety and efficacy against virulent exposure to *E. ictaluri*. No mortality following immersion exposure to each attenuated isolate was observed. Isolates 340Y and 340P were not shown to offer protection against virulent *E. ictaluri* challenge, regardless of exposure dose (Table 3.1). Post-challenge mortality of fish exposed to isolate 340X at an exposure dose of $5.2\times10^{+6}$, was significantly less than control fish and fish exposed to isolates 340Y and 340P. Based on these results, isolate S97-773-340X and related sub-isolets including S97-773-340X2 were evaluated for use as an oral vaccine.

Cultured isolates (340X, 340X1, 340X2, 340X3, 340X4, and 340X5) were diluted 1:10 and 1:100 with well water containing 1 g/L NaCl and mixed with feed at an inclusion rate of 100 ml/454 g of feed. Viable cell counts for the attenuated strain 340X after mixing were $8\times10^{+7}$ and $5\times10^{+6}$ /g of feed, respectively. Post-vaccination, pre-challenge mortality was negligible, and not statistically significant, in fish fed cultures diluted 1:10 and no mortality was observed in fish fed cultures diluted 1:100. Mortality was 1.0% in fish fed 1:10 dilutions of culture isolates 340X1 and 340X3. All treatment groups were shown to be significantly more resistant to *E. ictaluri* infection than control fish. Relative percent survival ranged between 94.2% and 100% for fish fed a 1:10 culture dilution and between 85.5% and 100% for fish fed a 1:100 culture dilution (Table 3.2). Master seed stock dilutions were prepared from culture isolates 340X and 340X2.

TABLE 3.1

Experiment 3. Initial screen of *Edwardsiella ictaluri* isolates demonstrating growth on media with a rifamycin concentration of 340 ul/ml. Fish were exposed to the isolates at varying concentrations (10 fold) by immersion exposure. Data represents percent mortality of non-exposed control fish and fish exposed to attenuated isolates following exposure to virulent *Edwardsiella ictaluri*. Isolates resulting in an RPS of > than 50% were considered effective.

| Approx Dose | Attenuated Isolates | | |
|---|---|---|---|
| (CFU/ml) | 340X | 340Y | 340P |
| $10^{+3}$ | 75 | 88 | 86 |
| $10^{+4}$ | 64 | 86 | 79 |
| $10^{+5}$ | 17 | 91 | 89 |
| (RPS) | (80%) | | |
| $10^{+6}$ | 0 | 85 | 90 |
| (RPS) | (100%) | | |

Mortality of control fish following virulent challenge = 82%

TABLE 3.2

Experiment 3. Safety and efficacy of orally delivered attenuated 340X isolates. Table data represents percent mortality of fish fed the attenuated cultures before and after exposure to virulent *Edwardsiella ictaluri*.

| | Safety | Efficacy | |
|---|---|---|---|
| Treatment | Pre-challenge Mortality | Post-challenge Mortality | RPS |
| 340X | | | |
| 1:10 dilution | 0.0 | 2.50 | 94.2% |
| 1:100 dilution | 0.0 | 1.25 | 97.1% |
| 340X1 | | | |
| 1:10 dilution | 1.25 | 1.25 | 97.1% |
| 1:100 dilution | 0.0 | 7.50 | 82.6% |
| 340X2 | | | |
| 1:10 dilution | 0.0 | 1.25 | 97.1% |
| 1:100 dilution | 0.0 | 2.50 | 94.2% |
| 340X3 | | | |
| 1:10 dilution | 1.25 | 0.0 | 100% |
| 1:100 dilution | 0.0 | 0.0 | 100% |
| 340X4 | | | |
| 1:10 dilution | 0.0 | 0.0 | 100% |
| 1:100 dilution | 0.0 | 7.50 | 82.6% |
| 340X5 | | | |
| 1:10 dilution | 0.0 | 0.0 | 100% |
| 1:100 dilution | 0.0 | 7.50 | 82.6% |

Mortality of control fish following exposure to virulent *E. ictaluri* = 43.3%

Experiment 4: Field Trials Evaluated Attenuated Isolate 340X as an Oral Vaccine.

Objective: To evaluate the safety and efficacy of attenuated isolate 340X2 delivered as an oral vaccine under commercial production conditions.

Methods

Studies were conducted in 0.1 acre ponds managed according to practices standard to the commercial culture of channel catfish fingerlings. Fish were obtained from a commercial catfish hatchery as sac-fry and maintained indoors under hatchery conditions. At the swim-up stage of development, fish were fed hourly a commercially-available fry feed. After 21 days, fish were stocked into 12, 0.1-acre ponds at a stocked rate of 10,000 fish per pond (100,000 fish per acre). Ponds were prepared and fish were raised according to practices typical of commercial operations. Throughout the study, ponds were fed and monitored daily for dead and moribund fish. Dead fish were removed and fish suitable for necropsy were evaluated to determine the cause of death.

Approximately 6 weeks after stocking, ponds were randomly assigned either a control or oral vaccine treatment. The average amount of feed consumed 1 week prior to vaccination was used to estimate the amount of feed fed on the day of vaccination. To increase feed consumption, fish were not fed two days before vaccination. In preparation of the oral vaccine, a culture of 340X2 was diluted 1:100 in well water containing 1 g/L NaCl and mixed with feed at a rate of 100 ml vaccine/1 lb (454 g) of feed. The vaccine/feed admix (400 ml/4 lb feed) was mixed until excess liquid was absorbed (approximately 1 min). Fish from each of the oral vaccine treatments were fed immediately after the oral vaccine was prepared. Ponds were fed within 5 min and feed consumption recorded. Non-vaccinated controls ponds were fed similarly but without the cultured isolate. Safety was assessed by observation of mortality 21 days post-vaccination.

When water temperatures were conducive for *E. ictaluri* infection, 1,000 albino channel catfish fingerlings were exposed to a virulent *E. ictaluri* culture and added to each pond. In addition, 1.5 L of the virulent *E. ictaluri* culture ($2.3\times10^{+9}$ CFU/ml) were added to each pond on 3 consecutive days (500 ml/pond/day). Based on the estimated pond volume, the pond inoculum delivered approximately $1\times10^{+4}$ CFU/ml of pond water. Dead fish were collected daily with a subsample evaluated and cultured for bacterial pathogens to determine cause of death. At the end of the production cycle (October, 2009), each pond was harvested to determine total survival and growth. Mortality, survival, fish biomass, feed conversion ratio and the dollar value of fish were used to assess production efficiency.

Results

Mortality or obvious signs of stress were not observed during the initial pond stocking. All ponds were accepting a floating catfish feed 21 days after stocking. Prior to delivery of the oral vaccine, the number of viable cells in the vaccine feed mixture was $1.9\times10^{+6}$ CFU/g feed. During delivery of the oral vaccine, feeding rates were at acceptable levels (average feed 3.8 lb/pond) with exception of one pond which consumed 2.8 lb. Following vaccination, no signs of disease or dead fish were observed among any of the oral vaccine treatments, indicating that oral delivery of the cultured isolate (340X2) of the present invention is safe for use in channel catfish fingerlings. The study was terminated and ponds harvested when pond water temperatures were less than 18° C.

Fish in the vaccinated and control treatments were consuming equal amounts of feed before ponds were inoculated with virulent *E. ictaluri*. With the onset of disease, feeding activity of control fish precipitously decreased but remained relatively constant in the vaccinated treatments (FIG. 1). In contrast to controls, vaccinated fish consumed similar quantities of feed before and after pond inoculation with *E. ictaluri*. Over the course of the study, vaccinated fish consumed 47% more feed than non-vaccinated fish and 157% more feed during the disease epizootic. Feed consumption was shown to decrease beginning in October, 2009 but this response was not disease-related and likely related to cooling pond water temperatures.

Figure 2:
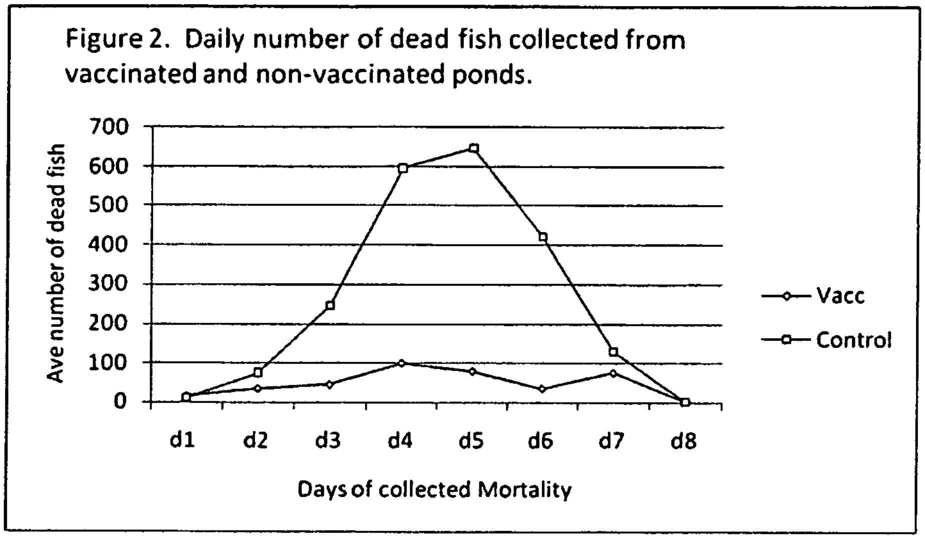
FIG. 2 is a graphical illustration of field trials of the daily number of dead fish collected from the vaccinated and non-vaccinated ponds.
Figure 3:
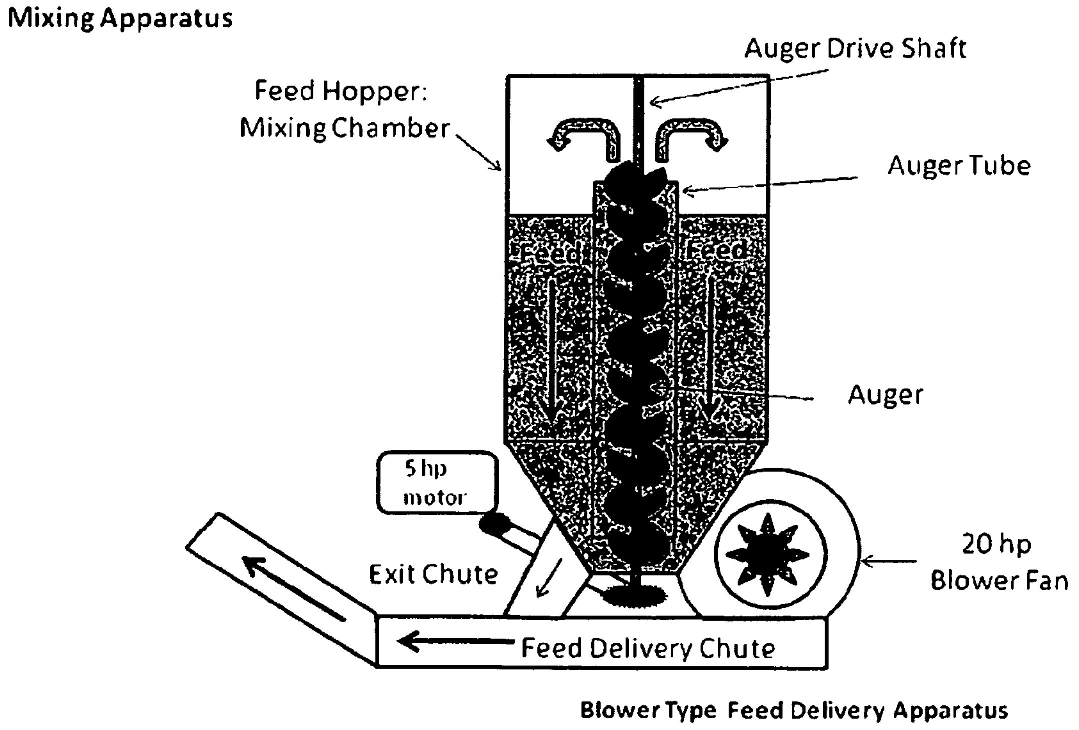
FIG. 3 is an illustration of the vaccine/feed mixing and delivery apparatus of the present invention.

The decrease in feeding activity of non-vaccinated fish signified the onset of disease. Mortality was first observed 6 days after ponds were inoculated with *E. ictaluri* and continued for approximately 8 days (FIG. 2). Initially gross clinical signs were suggestive of external *F. columnare* infection, but a majority of fish 2 days after the observance of mortality cultured positive for *E. ictaluri*. Within 1 week, gross clinical signs were consistent with *E. ictaluri* infection and external *F. columnare* infection, indicating the presence of mixed bacterial infections in a majority of fish. While *E. ictaluri/F. columnare* infection was identified in all ponds, mortality was significantly lower in ponds containing orally-vaccinated fish. Collected mortality of vaccinated fish was 3.2% compared to 20.7% in control fish, representing an RSP of approximately 84.5% (Table 4.1).

Increased feed consumption and decreased disease-related mortality associated with orally vaccinated fish translated to increased fish production and production efficiency at harvest (Table 4.1). Ponds containing vaccinated fish produced 91.9% more fish (4436 vs. 2311 fish/pond) of larger size (45.8 vs. 38.7 lbs/1000 fish) compared to non-vaccinated pond treatments, resulting in a 131% increase in total fish weight/pond. Additionally, vaccination significantly decreased feed conversion ratio from 2.24 to 1.33. Since feed is the largest variable cost to production, this represents a dramatic, increase in production efficiency. For example, given a feed cost of $350/ton, the cost of feed to produce 1 lb of vaccinated fish was $0.23 compared to a feed cost of $0.36 to produce the same weight of non-vaccinated fish, representing a 36.5% decrease in feed costs.

Gross fingerling sales (Table 4.2) were estimated based on production numbers generated from this study. Fish size in lbs/1,000 fish were converted to inches using available conversion tables used by commercial fingerling catfish producers (48 lb/1000 f=5.6 inches per fish and 38 lb/1000 f=5.2 inches per fish). Total inches of fish produced were multiplied by a typical commercial selling price of $0.01, $0.0125, and $0.015 per inch of fish. Given the number of fish produced in each treatment, gross sales on a per-acre basis (table values multiplied by 10) of vaccinated fish ranged between $2,481 to 3,726 and between $1,224 and $1,941 for non-vaccinated fish. At selling prices of $0.01, $0.0125, and $0.015 per inch, vaccination increased gross sales by $1,189, $1,487 and $1,785 per acre, respectively.

TABLE 4.1

Oral vaccination field trials. Harvest and production data of vaccinated and non-vaccinated fish raised in 0.1 acre ponds. Table data represents replicate pond observations for each parameter and treatment means.

| Treat Treat | No Fish Harv | Fish size lb/1000 fish | Harvest wt. lbs pond | Total[1] Feed fed(lbs) | Disease[2] Feed, fed(lbs) | FCR | Harvest[3] % surv | Collect[4] % mort |
|---|---|---|---|---|---|---|---|---|
| V1 | 4172 | 51.9 | 217 | 206 | 183 | 0.95 | 41.1 | 1.3 |
| V2 | 4959 | 41.3 | 205 | 266 | 153 | 1.30 | 49.3 | 0.5 |
| V3 | 3962 | 46.6 | 185 | 279 | 121 | 1.51 | 38.1 | 6.0 |
| V4 | 4384 | 39.8 | 174 | 242 | 135 | 1.39 | 42.7 | 4.6 |
| V5 | 3401 | 54.2 | 184 | 274 | 143 | 1.49 | 31.8 | 3.3 |
| V6 | 5738 | 41.32 | 237 | 324 | 98 | 1.37 | 57.4 | 3.3 |
| C1 | 2920 | 34.2 | 100 | 212 | 53 | 2.11 | 28.9 | 24.9 |
| C2 | 1877 | 39.5 | 74 | 144 | 78 | 1.94 | 18.1 | 16.3 |
| C3 | 2090 | 36.2 | 76 | 166 | 45 | 2.20 | 20.2 | 38.2 |
| C4 | 1018 | 49.0 | 50 | 184 | 35 | 3.68 | 10.0 | 19.4 |
| C5 | 3424 | 38.2 | 131 | 208 | 37 | 1.59 | 33.4 | 12.8 |
| C6 | 2539 | 35.3 | 90 | 171 | 76 | 1.91 | 24.5 | 12.7 |
| Means | | | | | | | | |
| Vac | 4436 | 45.8 | 200 | 265 | 138 | 1.33 | 43 | 3.2 |
| Con | 2311 | 38.7 | 87 | 181 | 54 | 2.24 | 23 | 20.7 |
| Diff | 2125 | 7.10 | 114 | 84 | 85 | (.90) | 20.9 | (17.5) |
| % Diff | 91.9 | 18.3 | 131 | 47 | 157 | (40.4) | 93 | (84.7) |
| PSEM | 399.2 | 2.345 | 10.482 | 13.645 | 10.412 | 0.231 | 0.035 | 0.0268 |
| P = | .0001 | 0.052 | 0.0001 | 0.0014 | 0.0001 | 0.016 | 0.008 | 0.005 |

[1]total feed fed/pond.

[2]Feed fed/pond with onset of mortality.

[3]% survival based on harvest head and stocking rate.

[4]% mortality based on number of dead fish removed from ponds and initial stocking rate.

Diff = difference between vaccinated and control values, (values) represent a decrease in value and percent decrease, PSEM = pooled standard error, of mean, P = probability level.

TABLE 4.2

Total inches of fish produced and gross sales of vaccinated and non-vaccinated fish. Gross sales/pond (0.10 acre) were determined on the inches of fish produced from each treatment multiplied by a selling cost of fingerlings of $0.01, $0.0125, and $0.0150. Total inches were determined by conversion table used by commercial producers to convert size of fish in lbs per 1,000 fish into inches. Table data represents total inches and gross sales for each pond and treatment means. At each selling value, vaccination increased gross sales by 91.9%.

| Treatment | Total inches Produced | Gross sales @ $0.010 | Gross sales @ $0.0125 | Gross sales @ $0.0150 |
|---|---|---|---|---|
| V1 | 23,363 | 233.6 | 292.0 | 350.4 |
| V2 | 27,768 | 277.7 | 347.1 | 416.5 |
| V3 | 22,189 | 221.9 | 277.4 | 332.8 |
| V4 | 24,551 | 245.5 | 306.9 | 368.3 |
| V5 | 19,043 | 190.4 | 238.0 | 285.7 |
| V6 | 32,131 | 321.3 | 401.6 | 482.0 |
| C1 | 16,349 | 163.5 | 204.4 | 245.2 |
| C2 | 10,510 | 105.1 | 131.4 | 157.7 |
| C3 | 11,705 | 117.0 | 143.3 | 175.6 |
| C4 | 5,699 | 57.0 | 71.2 | 85.5 |
| C5 | 19,174 | 191.7 | 239.7 | 287.6 |
| C6 | 14,215 | 142.2 | 177.7 | 213.2 |

TABLE 4.2-continued

Total inches of fish produced and gross sales of vaccinated and non-vaccinated fish. Gross sales/pond (0.10 acre) were determined on the inches of fish produced from each treatment multiplied by a selling cost of fingerlings of $0.01, $0.0125, and $0.0150. Total inches were determined by conversion table used by commercial producers to convert size of fish in lbs per 1,000 fish into inches. Table data represents total inches and gross sales for each pond and treatment means. At each selling value, vaccination increased gross sales by 91.9%.

| Treatment | Total inches Produced | Gross sales @ $0.010 | Gross sales @ $0.0125 | Gross sales @ $0.0150 |
|---|---|---|---|---|
| Mean | | | | |
| Vac | 24,841 | $248.4 | $310.5 | $372.6 |
| Cont | 12,942 | $129.4 | $161.8 | $194.4 |
| Diff | 11,899 | $119.0 | $148.7 | $178.5 |

The invention is described herein generically and in terms of specific examples, which are not intended as limiting unless specifically so indicated. The above detailed description is presented to enable any person skilled in the art to make and use the invention. Specific details have been revealed to provide a comprehensive understanding of the present invention, and are used for explanation of the information provided. These specific details, however, are not required to practice the invention, as is apparent to one skilled in the art. Descriptions of specific applications, analyses, and calculations are meant to serve only as representative examples. Various modifications to the preferred embodiments may be readily apparent to one skilled in the art, and the general principles defined herein may be applicable to other embodiments and applications while still remaining within the scope of the invention. There is no intention for the present invention to be limited to the embodiments shown and the invention is to be accorded the widest possible scope consistent with the principles and features disclosed herein.

What is claimed is:

1. A live attenuated cultured isolate of a strain of the gram negative enteric bacterium pathogen *Edwardsiella ictaluri* that is resistant to rifamycin and that protects fish from virulent isolate *E. ictaluri* strains and infection, wherein the live attenuated cultured isolate of a strain of *E. ictaluri* is selected from at least one or more of the sub-isolates of the attenuated culture S97-773-340X.

2. The isolate of claim 1, wherein the fish are catfish.

3. The live attenuated cultured isolate of a strain of the gram negative enteric bacterium pathogen *Edwardsiella ictaluri* of claim 1, wherein the isolate is the sub-isolate S97-773-340X2.

4. A vaccine composition comprising at least one protective dosage of the at least one live attenuated cultured isolate of the strain of *Edwardsiella ictaluri* of claim 1 and at least one carrier, wherein the composition is effective for protecting fish against infection from virulent *Edwardsiella ictaluri.*

5. The vaccine composition of claim 4, wherein the live attenuated cultured isolate of a strain of *E. ictaluri* is the sub-isolet S97-773-340X2.

6. The vaccine composition of claim 4, wherein the at least one carrier is water.

7. The vaccine composition of claim 4, wherein the at least one carrier comprises water, fish feed, or a combination thereof.

8. The isolate of claim 1, wherein the isolate is effective for protecting fish against virulent *Edwardsiella ictaluri* strains and infection when delivered to fish by immersion, injection, oral delivery, or a combination thereof.

9. The vaccine composition of claim 4, wherein the composition is effective for protecting fish against infection from virulent *Edwardsiella ictaluri* when delivered to fish by immersion, injection, oral delivery, or a combination thereof.

10. A method for protecting fish against infection from virulent pathogens in the genus *Edwardsiella*, the method comprising delivering the vaccine composition of claim 4 to the fish for oral consumption.

11. The method of claim 10, wherein the fish are catfish.

12. The method of claim 10, wherein the vaccine composition is mixed with and equally dispersed within the fish feed to form a fish feed mixture and wherein the fish feed mixture is delivered to the fish for oral consumption.

13. The method of claim 10, wherein delivering the vaccine composition protects fish against infection from virulent *Edwardsiella ictaluri.*

14. A method for protecting fish against infection from virulent pathogens in the genus *Edwardsiella*, the method comprising delivering the vaccine composition of claim 7 to the fish for oral consumption.

15. The method of claim 14, wherein the vaccine composition is mixed with and equally dispersed within the fish feed to form a fish feed mixture and wherein the fish feed mixture is delivered to the fish for oral consumption.

16. The method of claim 14, wherein delivering the vaccine composition protects fish against infection from any virulent *Edwardsiella ictaluri.*

17. The method of claim 10, wherein the at least one live attenuated cultured isolate of a strain of *E. ictaluri* is diluted to a protective dosage and mixed with fish feed at a concentration of about 100 ml/lb of feed to form a vaccine mixture.

18. The method of claim 17, wherein the attenuated isolate of a strain of *E. ictaluri* is diluted to a protective dosage with unchlorinated water.

19. The method of claim 17, wherein the oral consumption by the fish of the vaccine mixture occurs within about 15 minutes of mixing the diluted strain of *E. ictaluri* with fish feed.

20. A method for protecting fish against virulent pathogens in the genus *Edwardsiella*, the method comprising delivering the vaccine composition of claim 4 to the fish for oral consumption, wherein the vaccine composition is mixed with and equally dispersed within the fish feed and wherein the fish feed mixture is delivered to the fish for oral consumption.

21. The method of claim 20, wherein the virulent enteric infection or disease is *E. ictaluri.*

22. The method of claim 20, wherein the virulent enteric infection or disease is *E. tarda.*

23. An apparatus for delivering the vaccine composition of claim 4 to fish for oral consumption comprising:

- a hopper having a conical bottom portion for holding fish feed;
- an auger having a motor control and having multiple blades connected to a central rotatable auger drive shaft rotatably positioned in an auger tube in the center of the hopper, for mixing the fish feed and an oral vaccine to form a vaccine mixture;
- a connecting exit chute;
- a feed delivery chute;
- a means for delivering the vaccine mixture from the hopper through the connecting exit chute and to the feed delivery chute;
- a means for operating and rotating the auger in either a forward or reverse direction;

a blower fan for delivering the vaccine mixture from the feed delivery chute to a pond and to fish for oral consumption of the mixture;

a means within the hopper for controlling the quantity of vaccine mixture delivered to the feed delivery chute and to the fish; and a means for maintaining the moisture level of the original mixture containing fish feed and vaccine.

* * * * *